(12) United States Patent
Tsai et al.

(10) Patent No.: US 8,643,836 B1
(45) Date of Patent: Feb. 4, 2014

(54) INSPECTION METHOD FOR INSPECTING DEFECTS OF WAFER SURFACE

(75) Inventors: Hsin-Yi Tsai, Hsinchu (TW); Kuo-Cheng Huang, Hsinchu (TW); Ya-Cheng Liu, Hsinchu (TW); Min-Wei Hung, Hsinchu (TW)

(73) Assignee: National Applied Research Laboratories, Taipei (TW)

( * ) Notice: Subject to any disclaimer, the term of this patent is extended or adjusted under 35 U.S.C. 154(b) by 0 days.

(21) Appl. No.: 13/599,479

(22) Filed: Aug. 30, 2012

(51) Int. Cl.
*G01N 21/00* (2006.01)

(52) U.S. Cl.
USPC ..................... 356/237.5; 356/237.4

(58) Field of Classification Search
USPC .......... 356/237.1–237.6, 239.3, 239.7–239.8
See application file for complete search history.

(56) References Cited

U.S. PATENT DOCUMENTS

| 5,936,726 A * | 8/1999 | Takeda et al. .............. 356/237.2 |
| 6,084,664 A * | 7/2000 | Matsumoto et al. ....... 356/237.4 |
| 6,774,991 B1 * | 8/2004 | Danko ....................... 356/237.4 |

* cited by examiner

*Primary Examiner* — Tri T Ton
(74) *Attorney, Agent, or Firm* — Muncy, Geissler, Olds & Lowe, PLLC

(57) ABSTRACT

The present invention provides an inspection method for inspecting defects of wafer surface. The method includes: encircling peripheral region of the wafer surface by a first light source set and a second light source set; using a control module to control the first light source set and the second light source set to irradiate the light alternately from different directions; using an image pick-up module to receive a scattered light image during each time when the first light source set or the second light source set irradiates the light on the wafer surface; and then using a process module to obtain an enhanced and clear defect image of wafer surface by processing each of the scattered light images.

6 Claims, 11 Drawing Sheets

INSPECTION METHOD FOR INSPECTING DEFECTS OF WAFER SURFACE

BACKGROUND OF THE INVENTION

1. Field of the Invention

The present invention generally relates to an inspection method, in particular for inspecting defects of peripheral region of wafer surface by emitting linear light on a wafer surface.

2. Description of the Related Art

Owing to the non-single crystal lattice induced by a proper temperature change within the crucible, a lot of micro crystal defects (growth defects) will appear at the wafer surface. These growth defects often affect the behavior of carrier in the semiconductors. In the past, the inspection of growth defects could be performed by human eyes, but this method has some disadvantages such as lower accuracy and lower precision. Moreover, the human eyes will get tired after long term operation, so it cannot be widely used for the high speed and high repetition inspection. In order to improve these disadvantages, the automatic optical inspection (AOI) method is recently well recommended.

Generally, two system types are used to inspect the surface defects; the bright field (BF) system and the dark field (DF) system. The reflected light and scattered light from wafer surface is received by CCD camera in BF and DF system, respectively. During the inspection of growth defects by using the BF system, most of light will be reflected and acquired by the CCD camera, so the over-exposure image will be generated, which causes the surface defects are difficult to be observed. On the contrary, only the scattered light (about 5% of reflected light) induced by micro surface defects will be received by CCD camera in the DF system, and then the normal defects images can be readily obtained. However, the non-uniformity of brightness will be produced by using the DF method. The other disadvantages, such as bad image quality and inconvenient operation, are also caused.

SUMMARY OF THE INVENTION

Therefore, it is a primary objective of the present invention to provide an inspection method to improve the disadvantages such as non-uniformity of brightness, bad image quality and inconvenient operation.

To achieve the foregoing objective, the present invention provides an inspection method for inspecting defects of the wafer surface, wherein the wafer surface has a predetermined lattice orientation. The inspection method includes the following steps: encircling peripheral region of the wafer surface by a first light source set and a second light source set; using a control module to control the first light source set and the second light source set to irradiate the light alternately from different directions; using an image pick-up module to receive a scattered light image during each time when the first light source set or the second light source set irradiates the light on the wafer surface; and using a process module to obtain a defect image of wafer surface by processing each of the scattered light images.

Preferably, the first light source set may comprise a first light source and a third light source opposite to the first light source, the second light source set may comprise a second light source and a forth light source opposite to the second light source, and the step of using the control module may further comprise controlling the first light source and the third light source to irradiate light simultaneously, and then controlling the second light source and the forth light source to irradiate light simultaneously.

Preferably, by defining the intensity of the scattered image created by the first light source as $I_A$, the intensity of the scattered image created by the second light source as $I_B$, the intensity of the scattered image created by the third light source as $I_C$, and the intensity of the scattered image created by the forth light source as $I_D$, wherein the step of using the process module may further comprise performing the procedure $|(I_A+I_C)-(I_B+I_D)|$ to obtain the defect image of the wafer surface.

Preferably, the first light source set may comprise a first light source and a second light source adjacent to the first light source, the second light source set may comprise a third light source and a forth light source adjacent to the third light source, and the step of using the control module may further comprise controlling the first light source and the second light source to irradiate light respectively, and then controlling the third light source and the forth light source to irradiate light respectively.

Preferably, by defining the normalized intensity of the scattered image created by the second light source as $I_B^*$, the normalized intensity of the scattered image created by the third light source as $I_C^*$, and the intensity of the scattered image created by the forth light source as $I_D^*$ based on the average intensity of the scattered light image created by the first light source, wherein the step of using the process module may further comprise performing the procedure $|(I_A+I_C^*)-(I_B^*+I_D^*)|$ to obtain the defect image of the wafer surface.

Preferably, the first light source set and the second light source set may be the linear light source set.

Preferably, there is a predetermined angle between edge of the wafer and the first light source set or the second light source set and the step of using the control module may further comprise adjusting the predetermined angle according to the predetermined lattice orientation.

The inspection method for inspecting defects of wafer surface according to the present invention provides a simple inspection method which can adopted by proper inspection apparatus, wherein the present invention has the following advantages:

(1) The present invention provides a clear defect image of the wafer surface because the light source, such as linear light source, can uniformly irradiate the light on the peripheral region of the wafer surface. Therefore, the present invention can improve non-uniformity of brightness appear in prior art.

(2) The present invention provides better quality of defect image of the wafer surface by using the process module to process the scattered light image generated by the light sources, and derived from the image pick-up module, such as camera.

(3) The present invention provides more convenient operation method by substituting the inspection apparatus applied the inspection method of the present invention for human eyes.

BRIEF DESCRIPTION OF THE DRAWINGS

The detailed structure, an inspection method for inspecting the defects of the wafer surface of the present invention will now be described in more details hereinafter with reference to the accompanying drawings that show various embodiments of the invention as follows.

DETAILED DESCRIPTION OF THE PREFERRED EMBODIMENTS

The technical content of the present invention will become apparent by the detailed description of the following embodiments and the illustration of related drawings as follows.

Figure 1:
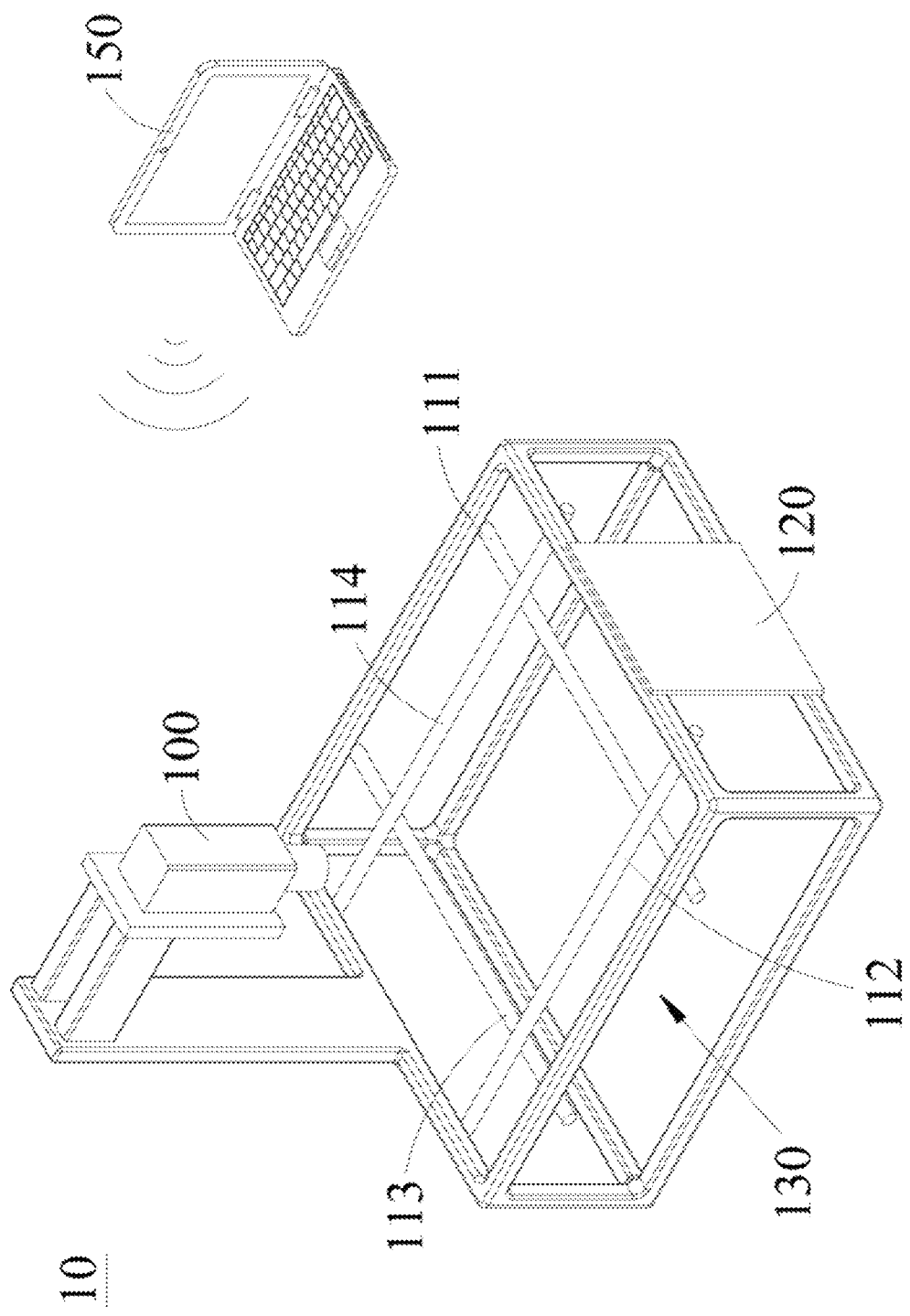
FIG. 1 is an apparatus applying the inspection method of the present invention.

With reference to FIG. 1 for an apparatus applying the inspection method of the present invention, the apparatus 10 includes a camera 100, a first light source 111, a second light source 112, a third light source 113, a forth light source 114, and a control module 120. In the inspection method of the present invention, the wafer can dispose in the accommodating space 130 of the apparatus 10 at low angle (about 15 to 30 degree), and arrange the edge of wafer with a predetermined angle relative to the first light source 111, the second light source 112, the third light source 113, or the forth light source 114.

The first, second, third and forth light source 111, 112, 113, and 114 in present invention preferably are linear line source for uniformly irradiating light on the peripheral region of the wafer surface. Furthermore, the first, second, third and forth light source 111, 112, 113, and 114 can be the light emitting diode (LED) light source, especially the white LED light, because the LED light has the advantages of longer lifetime, lower voltage and smaller volume, but is not limited thereto. In some cases, the first, second, third and forth light source 111, 112, 113, and 114 in present invention can replace with red LED light source, yellow LED light source or even the laser light source or the halogen lamp.

Figure 2:
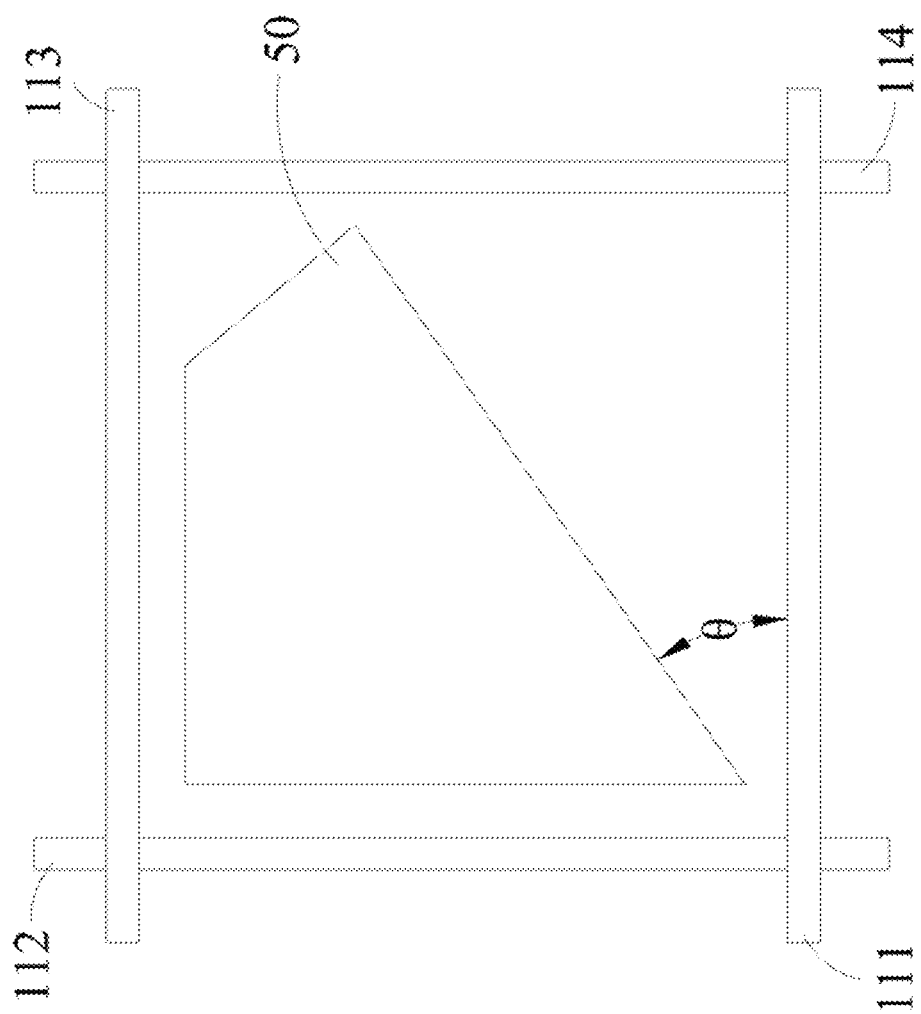
FIG. 2 is a vertical view of an apparatus applying the inspection method of the present invention.

With reference to FIG. 2 for a vertical view of an apparatus applying the inspection method of the present invention, the wafer 50 is placed in the accommodating space 130 shown in FIG. 1. In order to make the defects on the peripheral region of wafer surface can be detected more clearly, the edge of the wafer surface should be disposed with a predetermined angle θ related to the first light source 111. The predetermined angle θ can be adjusted according to a predetermined lattice orientation of the wafer, because when the first, second, third or forth light source 111, 112, 113, or 114 irradiates light on the peripheral region of the wafer surface, the reflected light may response mostly in some lattice orientation.

For an example, when the orientation of the present example is (100) defined by the Miller index, the predetermined angle θ is about 33 degree between the first light source 111 and the edge the wafer 50, but is not limited thereto. When the orientation of is (110), or (111) or some other directions in other examples, the predetermined angle θ can be adjusted respectively according to the lattice orientation.

After placing the wafer 50 in the preferable position in the accommodating space 130, and adjusting the predetermined angle θ to have the obviously reflected light, the control module 120 then control the first, second, third, and forth light source 111, 112, 113, and 114 to irradiate the light simultaneously or separately to create a plurality of the scattered light image derived by the camera 100, and a process module 150 can obtain a defect image of the peripheral region of the wafer surface by processing those scattered light images.

More specifically, in the present invention, there is several ways to obtain the different scattered light images for generating the defect image by process module 150. In an exemplary embodiment, the control module 120 can controls the first light source 111, the second light source 112, the third light source 113, and the forth light source 114 separately or sequentially to irradiate the light on the peripheral region of the wafer surface, and then the camera 100 can derive four scattered light images corresponding to each of the first light source 111, the second light source 112, the third light source 113, and the forth light source 114.

Figure 3A:
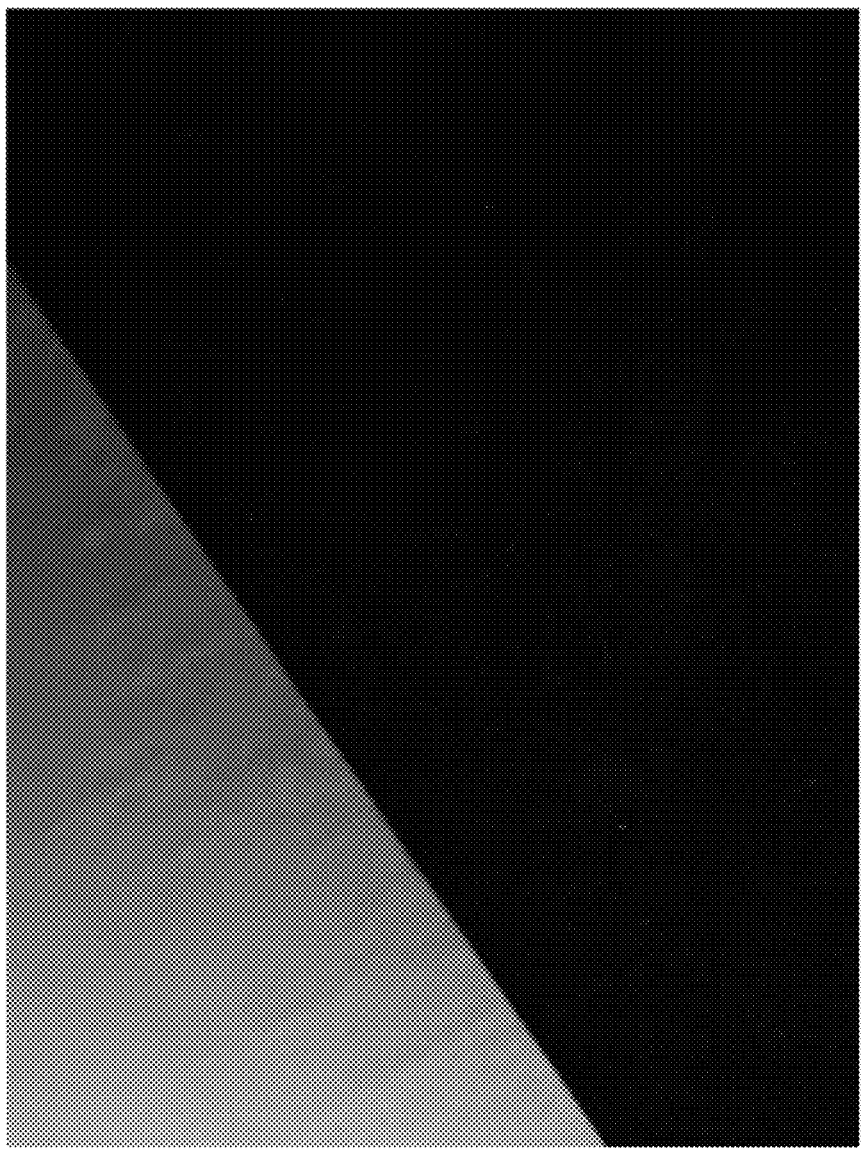
FIG. 3A to 3D are scattered light images generated from four light sources.
Figure 3B:
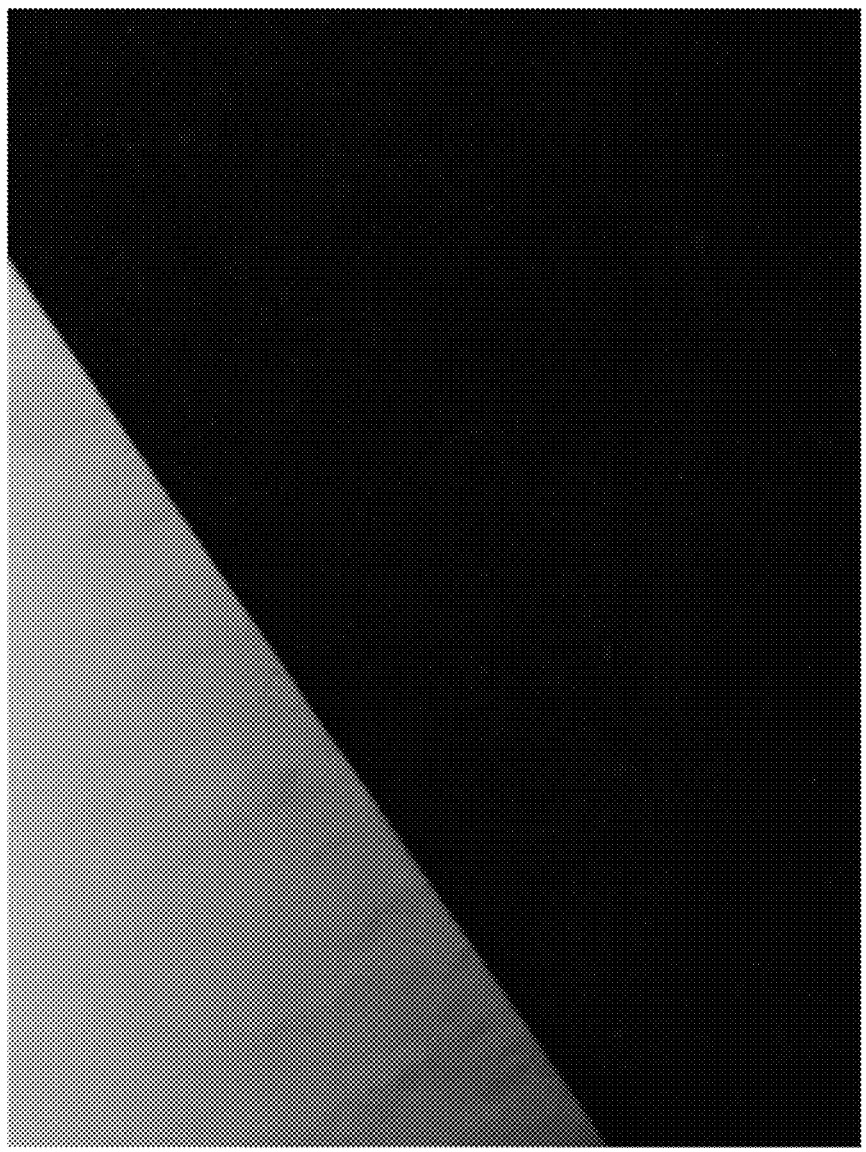
Figure 3C:
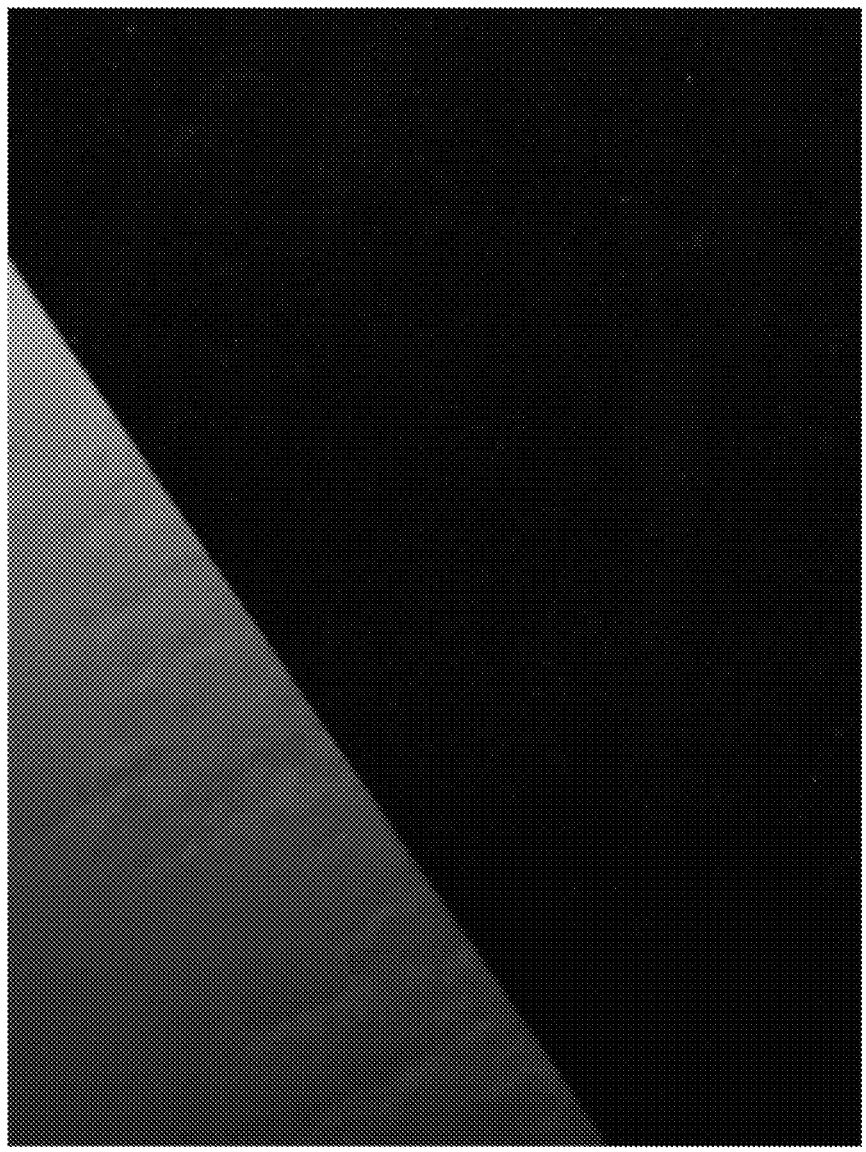
Figure 3D:
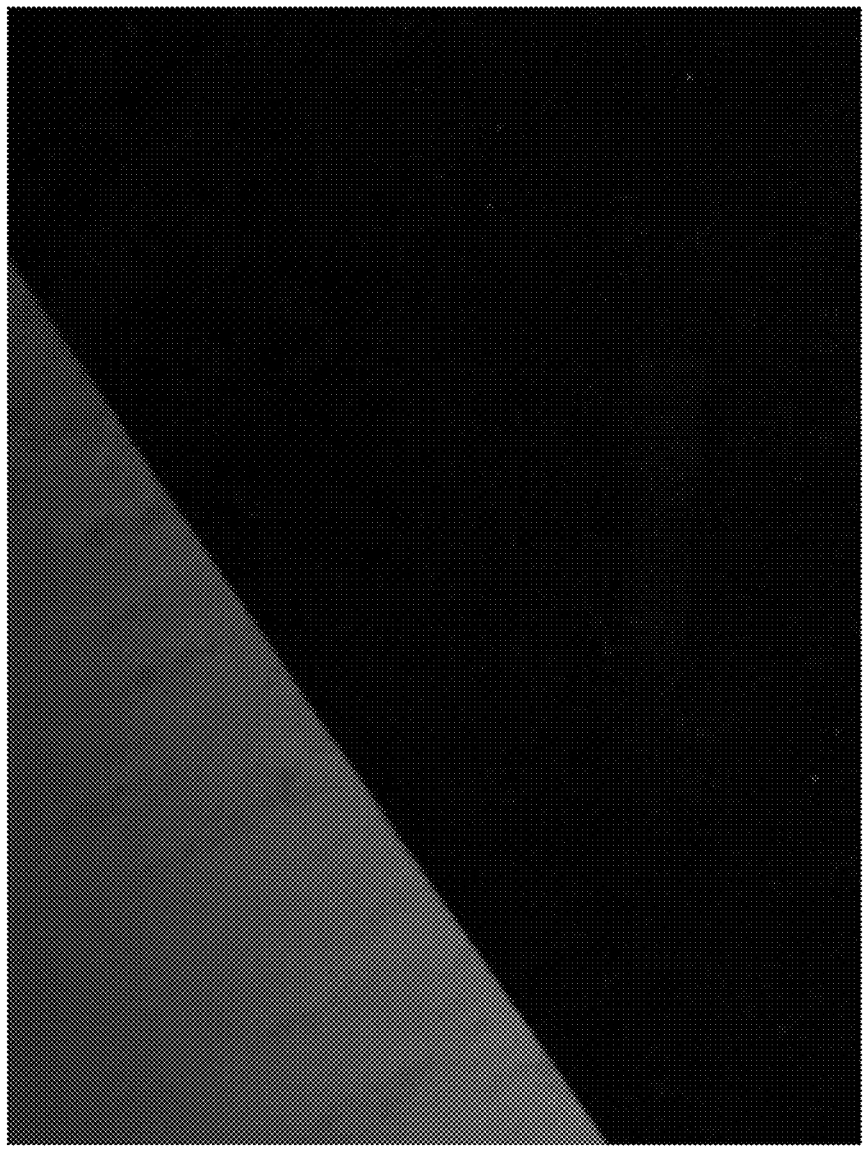

For more complete understanding, a real photos derived from the camera 100 according to the present exemplary embodiment are provided in FIGS. 3A, 3B, 3C, and 3D. FIG. 3A is the scattered light image while the second light source 112 irradiates light on the peripheral region of the wafer surface. FIG. 3B is the scattered light image while the third light source 113 irradiates light on the edge of the wafer surface. FIG. 3C is the scattered light image while the forth light source 114 irradiates light on the edge of the wafer surface. FIG. 3D is the scattered light image while the first light source 111 irradiates light on the edge of the wafer surface. It is should be noted that the scattered light images generated by single light source is already able to observe the defects on the peripheral region because of the un-uniform reflected light scattered by defects.

Figure 4:
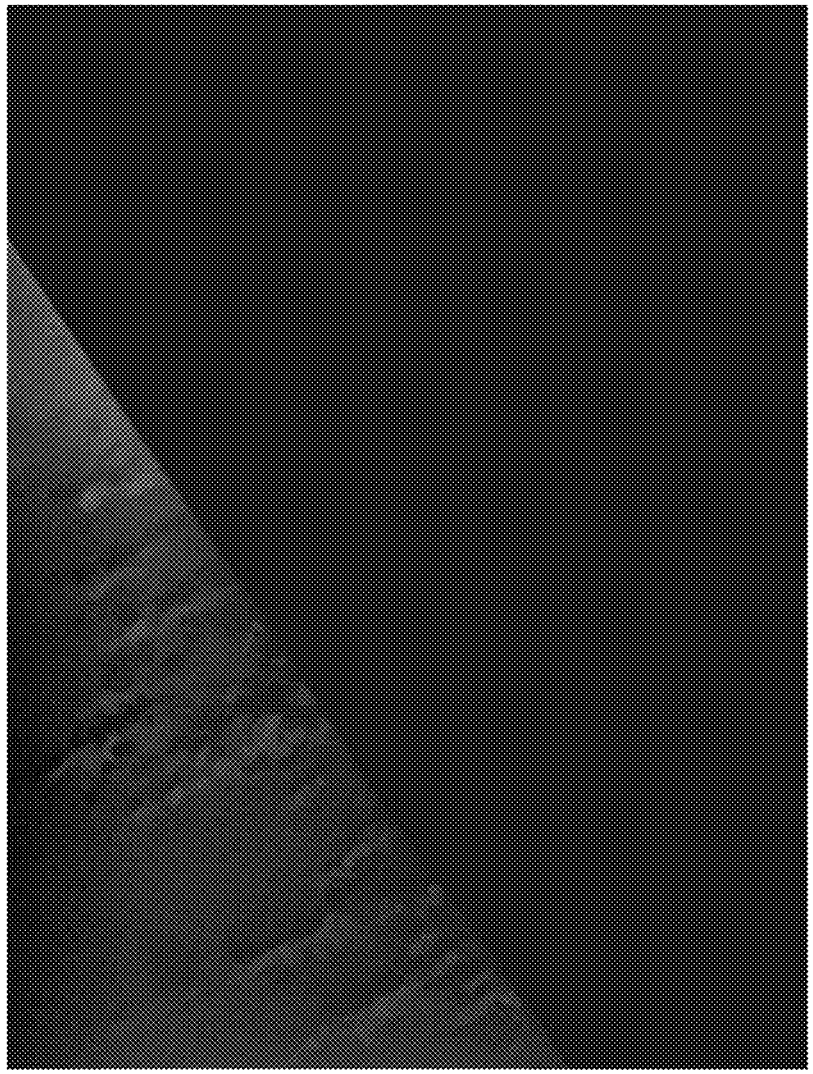
FIG. 4 is a scattered light image by processing the images of FIG. 3A to 3D.

Next, for obtaining more apparent image of peripheral region defect of the wafer surface, the process module 150 can perform some image process. First, based on the same average intensity as the image of FIG. 3A which expressed as $I_A$, the intensity of the images of FIGS. 3B, 3C and 3D can be normalized and expressed as $I_B^*$, $I_C^*$ and $I_D^*$, and then performing a procedure $|(I_A+I_C^*)-(I_B^*+I_D^*)|$ to obtain the defect image of the wafer surface as shown in FIG. 4. With reference to FIG. 4, an apparent and clear defect image where the defects of less than 50 μm and the ripple of defects can be obviously observed.

In another exemplary embodiment, the control module 120 can control the first light source 111 and the third light source 113 irradiate the light on the peripheral region of the wafer surface simultaneously, and then control the second light source 112 and the forth light source 114 irradiate the light on the peripheral region of the wafer surface simultaneously. At the time when the first light source 111 and the third light source 113 irradiating the light, the camera 100 can derive a scattered light image relate to the peripheral region of the wafer surface, and when the second light source 112 and the forth light source 114 irradiate the light, the camera 100 can derive another scattered light image relate to the peripheral region of the wafer surface.

Figure 5A:
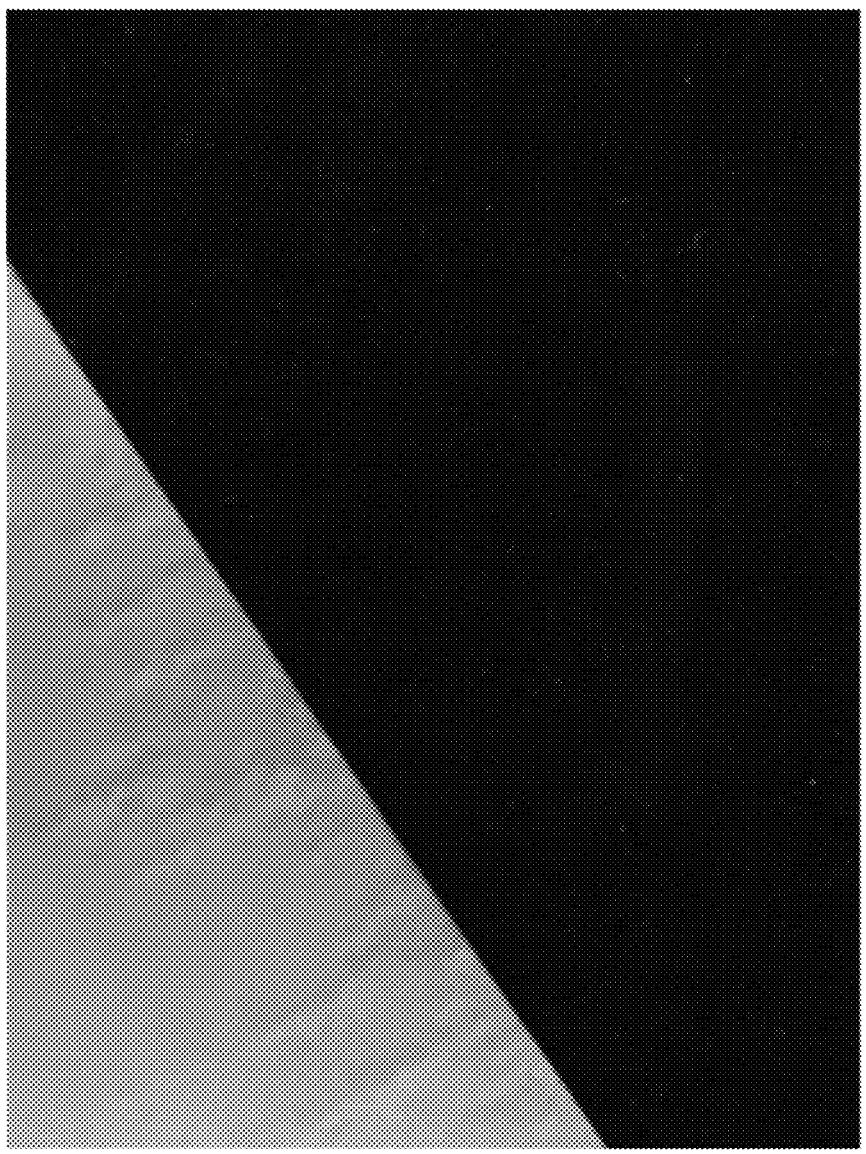
FIGS. 5A and 5B are scattered light images generated from two light sources set.
Figure 5B:

For more complete understanding, a real photos derived from the camera 100 according to the present exemplary embodiment are provided in FIG. 5A and FIG. 5B. FIG. 5A is the scattered light image while the second light source 112 and the forth light source 114 irradiate the light on the peripheral region of the wafer surface. FIG. 5B is the scattered light surface while the first light source 111 and the third light source 113 irradiate the light on the peripheral region of the wafer surface. It is should be noted that the scattered light image generated by two light source also can observe the defects on the peripheral region because of the un-uniform reflected light scattered by defects.

Figure 6:
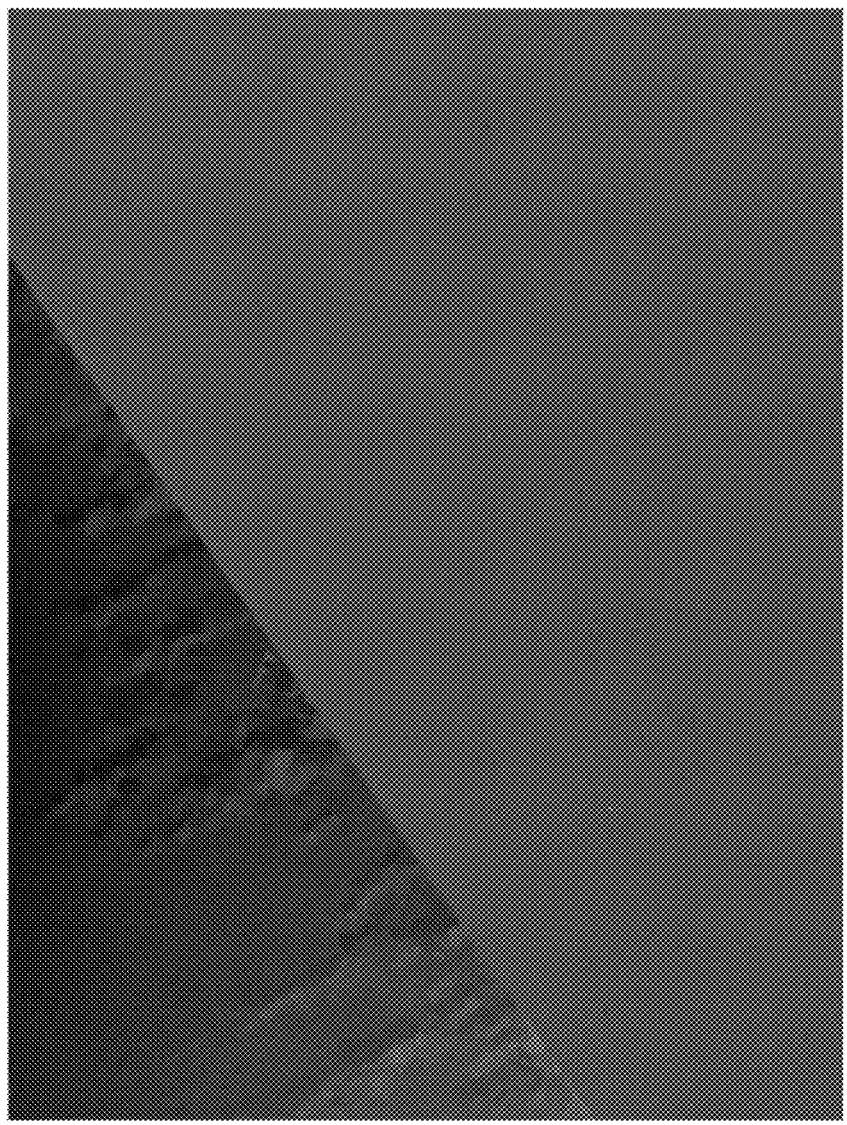
FIG. 6 is a scattered light image by processing the images of FIGS. 5A and 5B.

Next, in order to get the enhanced and clarity image of the peripheral region of the wafer surface, the process module 150 can perform some image process. First, defining the intensity of the scattered light image while first light source 111 and the third light source 113 irradiating the light as $I_A+I_C$, and defining the intensity of the scattered light image while second light source 112 and the forth light source 114 irradiating the light as $I_B+I_D$. Then performing a procedure $|(I_A+I_C)-(I_B+I_D)|$ to obtain the defect image of the wafer surface as shown in FIG. 6. With reference to FIG. 6, though the distribution of light intensity of defects image is a little inconsistent, a clarity and enhances defect image can be obtained by using the present exemplary embodiment.

Figure 7:
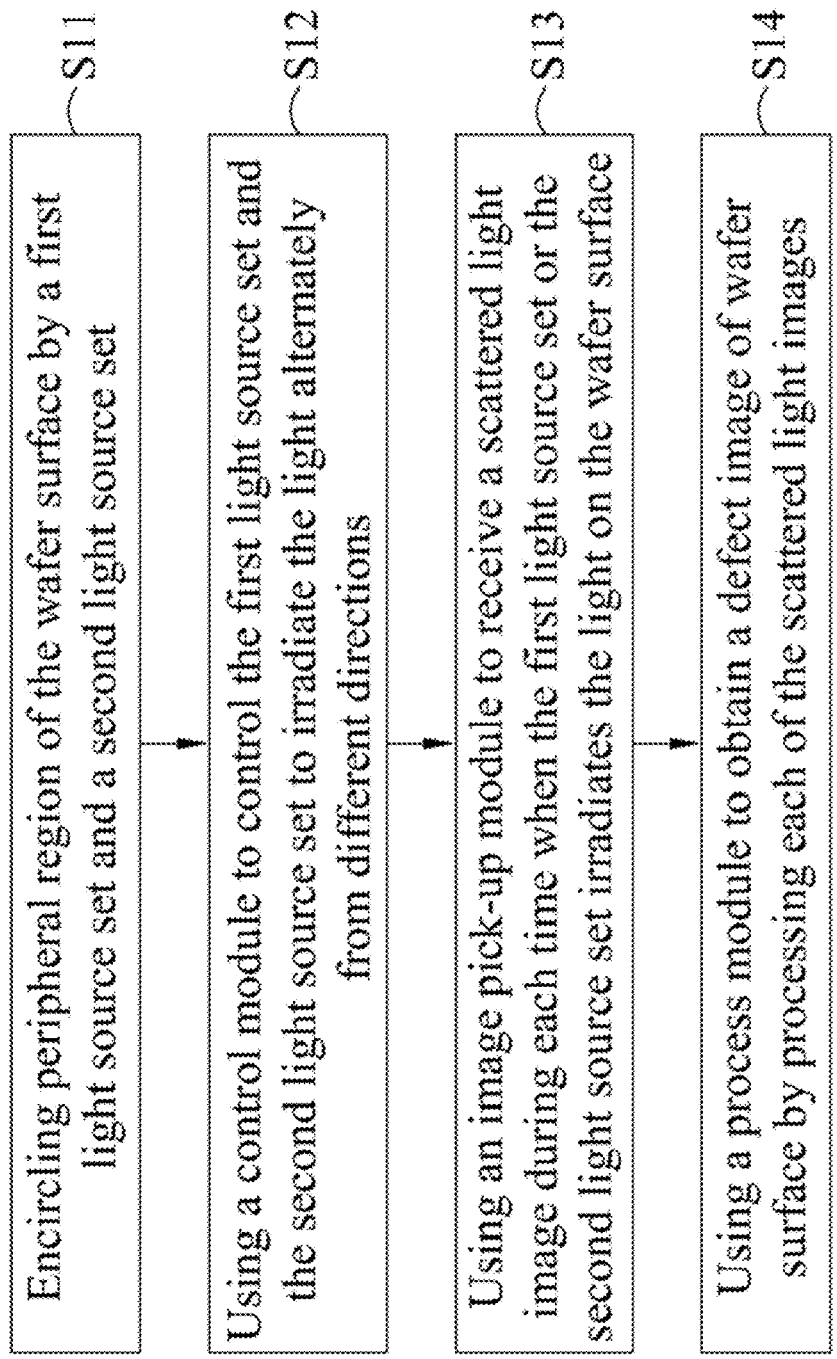
FIG. 7 is a flow process of the inspection method for inspecting defects of the wafer surface according to the present invention.

With reference to FIG. 7 for a flow process of the present invention, the inspection method for inspecting defects of the wafer surface includes the following steps.

S11: encircling peripheral region of the wafer surface by a first light source set and a second light source set, wherein as shown in FIG. 1 and FIG. 2, the first light source set can include a first light source and a second light source, a second light source set can include a third light source and a forth light source, or the first light source set can include a first light source and a third light source, the second light source set can include a second light source and a forth light source, but is not limited thereto. In some embodiments, the first light source set or the second light source set can have more than two light sources.

It is should be noted that the light source set of the present invention can be a linear light source set, but is not limited thereto. In some embodiments, light sources that can uniformly irradiate the light on the peripheral region of the wafer surface can substitute for the first light source set or the second light source set.

Furthermore, there should be a predetermined angle between edge of the wafer and the first light source set or the second light source set, so as to have better reflect reaction when light irradiates on the peripheral region of the wafer surface. Wherein, the predetermined angle can be adjusted according to the lattice orientation of the wafer.

S12: using a control module to control the first light source set and the second light source set to irradiate the light alternately from different directions, wherein the present invention mainly provides at least two different direction of light beam to irradiate on the peripheral region of the wafer surface, so that to generate at least two different scattered light images.

More specifically, in some exemplary embodiments, the control module can control two light sources opposite to each other to irradiate light simultaneously, and then control another two light sources opposite to each other to irradiate light simultaneously to generate two different scattered light images, but is not limited thereto. In other exemplary embodiments, the control module can control two light sources adjacent to each other to irradiate light respectively, and then control another two light sources adjacent to each other to irradiate light respectively, so that to generate four different scattered light images.

S13: using an image pick-up module to receive a scattered light image during each time when the first light source set or the second light source set irradiates the light on the wafer surface.

S14: using a process module to obtain a defect image of wafer surface by processing each of the scattered light images, wherein in some exemplary embodiments, the process module can subtract the scattered light image created by two light source opposite to each other from the scattered light image created by another two light source opposite to each other, but is not limited thereto. In other exemplary embodiments, the process module can firstly base on one scattered light image created by single light source to normalize three different scattered light images created by three different light sources, and then performing the procedure such as $|(I_A+I_C{}^*)-(I_B{}^*+I_D{}^*)|$ described in former paragraph to obtain the defect image of the wafer surface.

In summary, the present invention provides a clear defect image of the wafer surface because the light source can uniformly irradiate the light on the peripheral region of the wafer surface. Moreover, the present invention can provide a large inspection zone and rapid inspection speed due to using the linear light source and using the camera to derive the scattered light image. At last, the present invention can decrease the cost because of using the light source such as LED light, and only need to properly process the scattered light images created by the LED light to obtain the defect image of the peripheral region of the wafer surface.

While the means of specifications and variations could be made thereto by those skilled in the art without departing from the scope and spirit of the invention set forth in the claims. The modifications and variations should in a range limited by the specification of the present invention.

What is claimed is:

1. An inspection method for inspecting defects of wafer surface, wherein the wafer surface has a predetermined lattice orientation, the method comprising:

encircling peripheral region of the wafer surface by a first light source set and a second light source set;

using a control module to control the first light source set and the second light source set to irradiate light alternately from different directions;

using an image pick-up module to receive a scattered light image during each time when the first light source set or the second light source set irradiates the light on the wafer surface; and using a process module to obtain a defect image of the wafer surface by processing each of the scattered light images;

wherein the first light source set comprises a first light source and a third light source opposite to the first light source, the second light source set comprises a second light source and a forth light source opposite to the second light source, and the step of using the control module further comprises controlling the first light source and the third light source to irradiate the light simultaneously, and then controlling the second light source and the forth light source to irradiate the light simultaneously.

2. The inspection method of claim 1, defining intensity of the scattered image created by the first light source as $I_A$, intensity of the scattered image created by the second light source as $I_B$, intensity of the scattered image created by the third light source as $I_C$, and intensity of the scattered image created by the forth light source as $I_D$, wherein the step of using the process module further comprises performing a procedure $|(I_A+I_C)-(I_B+I_D)|$ to obtain the defect image of the wafer surface.

3. An inspection method for inspecting defects of wafer surface, wherein the wafer surface has a predetermined lattice orientation, the method comprising:

encircling peripheral region of the wafer surface by a first light source set and a second light source set;

using a control module to control the first light source set and the second light source set to irradiate light alternately from different directions;

using, an image pick-up module to receive a scattered light image during each time when the first light source set or the second light source set irradiates the light on the wafer surface; and using a process module to obtain a defect image of the wafer surface by processing each of the scattered light images;

wherein the first light source set comprises a first light source and a second light source adjacent to the first light source, the second light source set comprises a third light source and a forth light source adjacent to the third light source, and the step of using the control module further comprises controlling the first light source and the second light source to irradiate light respectively, and then controlling the third light source and the forth light source to irradiate the light respectively;

wherein the method defines normalized intensity of the scattered image created by the second light source as $I_B^*$, normalized intensity of the scattered image created by the third light source as $I_C^*$, and intensity of the scattered image created by the forth light source as $I_D^*$ based on average intensity of the scattered light image created by the first light source, wherein the step of using the process module further comprises performing a procedure $|(I_A+I_C^*)-(I_B^*+I_D^*)|$ to obtain the defect image of the wafer surface.

4. The inspection method of claim 1, wherein the first light source set and the second light source set are linear light source set.

5. The inspection method of claim 1, wherein there is a predetermined angle between edge of the wafer and the first light source set or the second light source set.

6. The inspection method of claim 5, wherein the step of using the control module further comprises adjusting the predetermined angle according to the predetermined lattice orientation.

* * * * *